United States Patent [19]

Wallace

[11] Patent Number: 4,938,747
[45] Date of Patent: Jul. 3, 1990

[54] BODY LIQUID DRAINAGE DEVICE

[75] Inventor: Stephen J. Wallace, Colchester, United Kingdom

[73] Assignee: Medical Assist Limited, United Kingdom

[21] Appl. No.: 281,209

[22] Filed: Dec. 8, 1988

[30] Foreign Application Priority Data

Dec. 9, 1987 [GB] United Kingdom ............... 8728773

[51] Int. Cl.⁵ .......................................... A61M 1/00
[52] U.S. Cl. .................................. 604/317; 604/327; 604/323
[58] Field of Search ................. 604/317, 322–327, 604/410, 411; 128/760, 767; 383/2, 38

[56] References Cited

U.S. PATENT DOCUMENTS

| | | | |
|---|---|---|---|
| 3,228,444 | 1/1966 | Weber et al. | 604/317 |
| 3,601,119 | 8/1971 | Engelsher | 604/323 |
| 4,319,573 | 3/1982 | Whitlock | 604/323 |
| 4,625,734 | 12/1986 | Sherlock et al. | 604/325 |

Primary Examiner—J. L. Kruter
Attorney, Agent, or Firm—Frank P. Presta

[57] ABSTRACT

The invention provides a body liquid drainage device (9) particularly for urine, said device comprising a first liquid storage chamber (20) formed of a flexible plastics material and provided with an upper inlet (1) for body liquids, and a lower valved outlet (12) for body liquids.

A second liquid storage chamber (10) is operatively connected to the first liquid storage chamber (20) and is selectively fillable. Preferably said second chamber is moveable from a first position in which it is generally in parallel abutment with the first chamber thereby to overlie the same; to a second position in which it forms an extension of the first chamber. The device may be utilized in a lower capacity mode during daytime, and in a higher capacity second mode in non-ambulant times or during night-time.

This arrangement prevents invasive infections occurring because inter-connection between in-dwelling catheter and the drainage bags are infrequent.

10 Claims, 3 Drawing Sheets

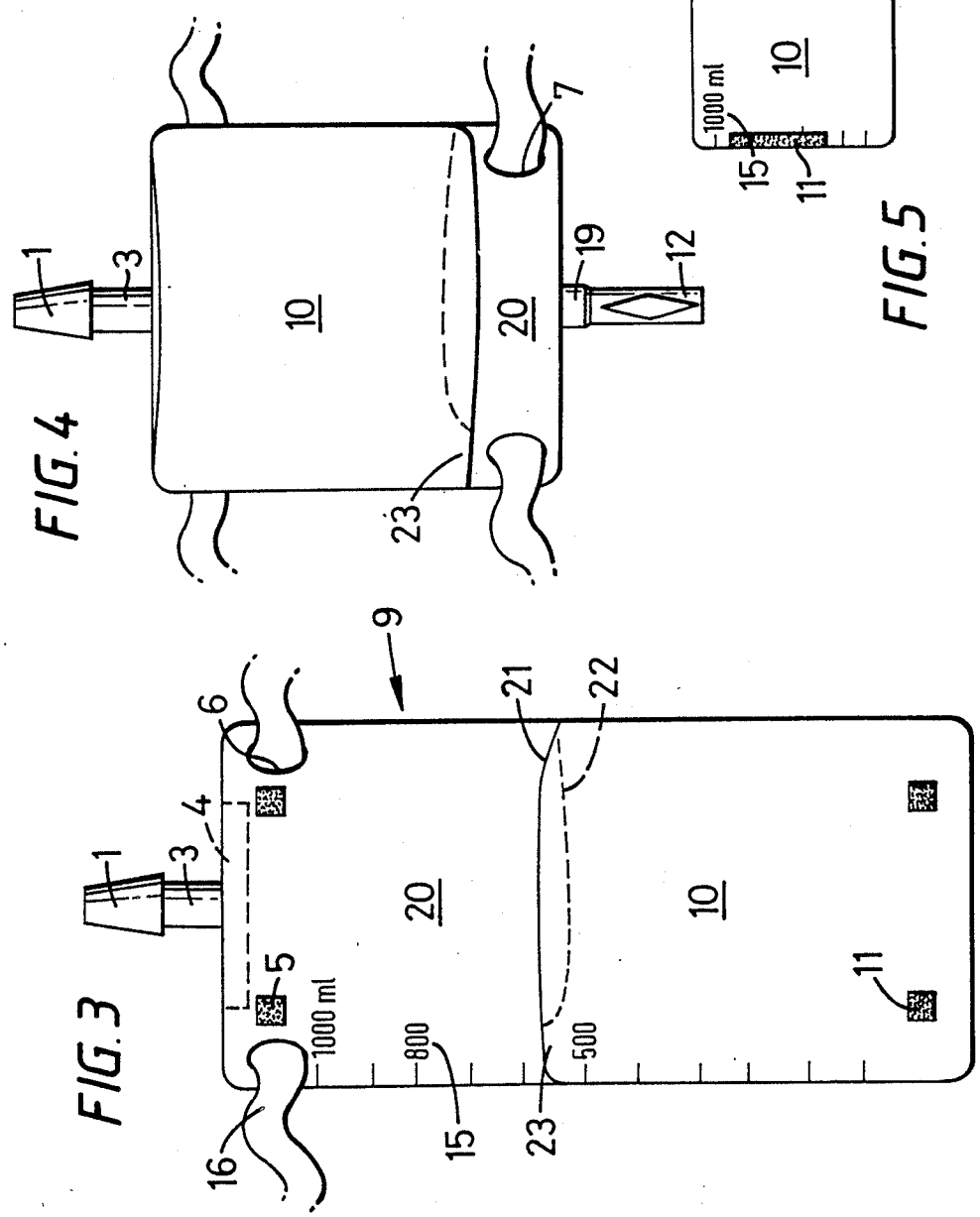

BODY LIQUID DRAINAGE DEVICE

BACKGROUND OF THE INVENTION

The present invention relates to a body liquid drainage device, particularly a urinary drainage device. It also relates to a method for preventing counter-current infection from such devices.

Artificial drainage of urine from the bladder is necessary when incontinence exists or when the natural process for draining the bladder is impaired or interrupted. Thus, for example, natural drainage may be interrupted in the male by pre-operative retention of urine due to an enlarged prostate or by post-operative impairment of sphincter function due to surgery of prostatic tissue. Similarly, in the female, natural drainage can be interrupted after gynaecological surgery.

Artificial drainage can be achieved by introducing a tube (a catheter) into the bladder via the urethra and the catheter may be withdrain after emptying of the bladder. Alternatively, it may be retained and connected to a length of tubing attached to a drainage bag so that the urine can be drained continuously.

In a post-operative situation a suitable drainage system is critical to the successful recovery of the patient, and in order to maintain efficient drainage, usually under gravity, the catheter and tubing must both be correctly placed and correctly maintained in position so that there is no impairment of the flow of urine. If the flow of urine is impaired or shut off, retention of urine in the bladder results, with subsequent retrograde invasion of the ureters and kidneys by bacteria passing up from the bladder.

For overnight urine drainage in a patient with either a catheter or an external appliance, it is important that the overall drainage capacity of any system employed should be sufficient to accommodate the amount of urine likely to drain from the patient while asleep. In that situation, it has been generally known to utilise one of the following systems:

For day drainage the semi-ambulant/ambulant patient is provided each morning with a leg bag secured to the patient. Each evening the leg bag is removed and the patient is connected for the night to a bedside drainage bag on a stand. This system is acceptable in that the leg bag can be worn discreetly and the patient can be relatively mobile during the day. However, the system involves the disadvantage of necessitating the breaking of the closed drainage circuit each morning and each evening, with consequent risk of contamination each time the circuit is broken. In this respect it is to be noted that at least 30% of all hospital acquired infections are urinary tract related.

Alternatively, the patient may be permanently connected to a bedside drainage bag. This avoids breaking the closed circuit twice daily, but leaves the patient to carry a large bag and stand about if mobility is required, which makes rehabilitation difficult. Furthermore, use of the night drainage bag during the day acts as a visual reminder to the patient of his or her current condition and increases psychological trauma, especially in the case of more mobile patients who are ambulant or in wheelchairs.

It is now more common to permit patients to wear their leg bag at night and to connect the leg bag outlet, rather than the catheter, to a bedside disposable night bag (described in European Patent Application No. 85301059.3).

This eliminates the need for disconnecting the leg bag from the catheter or the like, with consequent connection of a bedside drainage bag, thus reducing the likelihood of urinary tract infection due to contamination when the closed system is broken.

The third technique described above is now the most preferred method of night drainage and has encouraged greater use than ever of leg bags for day drainage, where previously hospital infection control policies may have prevented the use of leg bags as it implied breaking the closed circuit twice daily to convert to and from a night bag. However, this system is not entirely satisfactory for the reasons summarised below:

1. Handling of the junction between the leg bag outlet tap and the night bag increases the risk of hand contamination of urine.
2. The risk of cross-infection is increased through handling.
3. The task of handling the system has to be carried out by a nurse or nursing auxilliary and therefore consumes other people's time and in any event does not encourage self-help by the patient.
4. If the procedure is not carried out correctly, serious problems can arise, namely if the tap of the leg bag is not opened to drain at night or closed after disconnection in the morning, leakage of urine will occur. Similarly, if a good connection is not made between the leg bag outlet tap and the night bag, leakage of urine will occur.
5. The presence of a night drainage bag placed at the bedside does not help ease the psychological trauma of the patient.
6. Stocks of leg bags and night bags must be available at all times, because the night bag is discarded with its contents each morning.

SUMMARY OF THE INVENTION

According, therefore, to a first aspect of the present invention there is provided a body liquid drainage device comprising a first liquid storage chamber formed of a flexible plastics material, and provided with an upper inlet for body liquids and a lower valved outlet for body liquids, characterised by a second liquid storage chamber operatively connected to the first liquid storage chamber, said second chamber being configured for selective operation so as to be filled with the body liquid only when desired. Preferably the second chamber is moveable from a first position in which it is generally in parallel abutment with the first chamber thereby to overlie the same in use, to a second position in which it forms an extension of the first chamber.

In the second aspect of the invention there is provided a method for the prevention of retrograde infection from a body liquid storage bag, which method comprises causing the body liquid to flow into a first chamber provided with a valved outlet, said first outlet being sized for ambulant use, characterised by the provision of a second chamber of a generally equivalent size operatively connected to said first chamber and being adapted to be filled by said liquid in a non-ambulant mode concurrently or consecutively with said first chamber.

In a preferred embodiment the second chamber is emptiable with the first chamber in situ on a patient, said emptying manoeuvre being effected by pivotal action about the point of conjunction between the first and second chambers whereby the second chamber can be emptied without disconnection or use of a second valve.

It will be noted that in the second position the valved outlet from the first chamber maybe positioned intermediate the length of the device so that only by pivoting the second chamber upwardly can the liquid contents of the second chamber be expelled via the valve.

The device is preferably provided with releaseable retaining means, secured to co-operating surfaces of the first and second chambers thereby to fix said chambers into overlying abutment in use in the ambulant mode.

The present invention thus provides a body liquid drainage device which is attached to the patient with either leg straps or by means of a waist suspension system or similar means. In the device of the invention a non-return valve is preferably incorporated to the upper inlet for body liquids to prevent the reflux of urine into the bladder.

In the device of the invention the drainage bag may be welded to form two chambers, the operative interconnection therebetween being created by a break in the weld.

BRIEF DESCRIPTION OF THE DRAWINGS

The invention will now be described, by way of illustration only, with reference to the accompany drawings wherein:

FIGS. 3 and 4 show alternative embodiments to the arrangement of FIGS. 1 and 2 and FIG. 5 shows an arrangement whereby the second bag extends laterally.

DESCRIPTION OF THE PREFERRED EMBODIMENT

Figure 1:
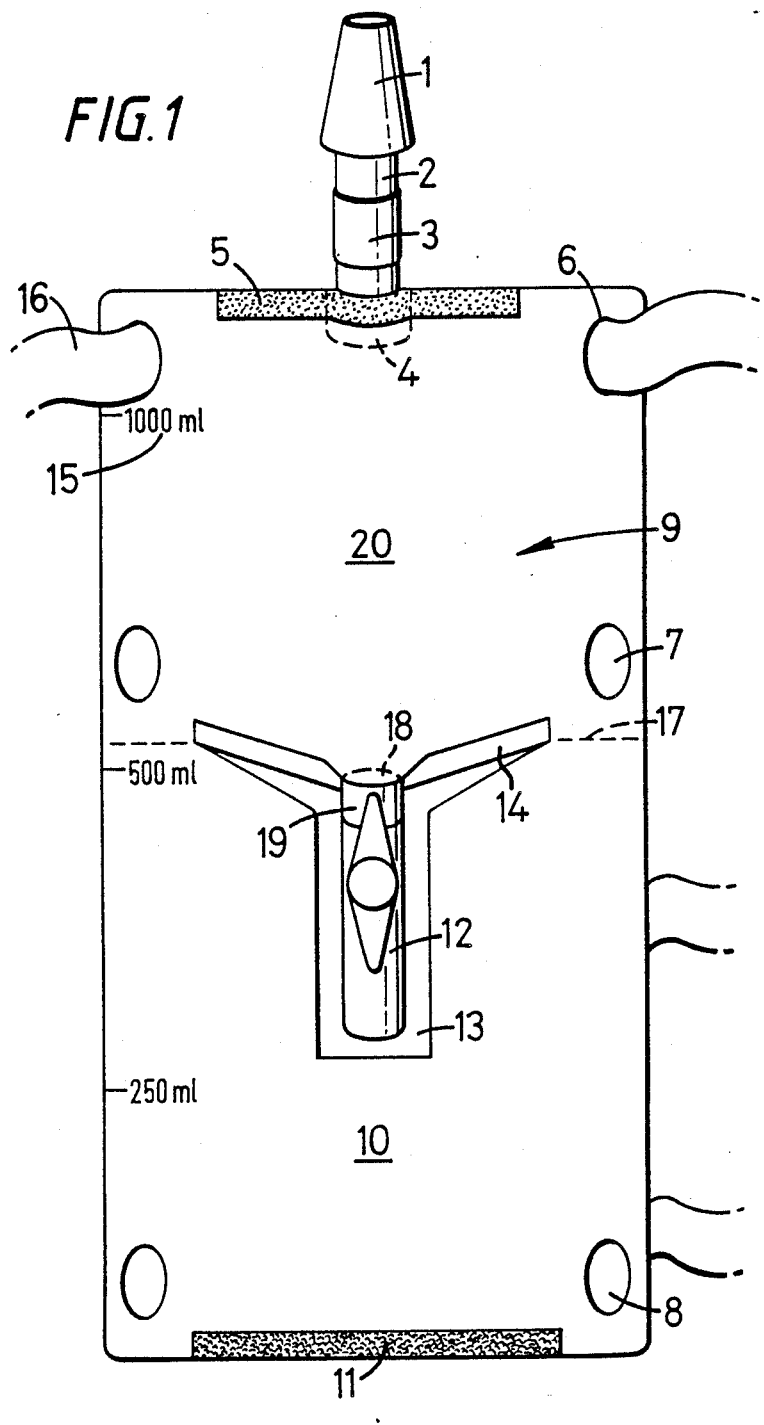
FIG. 1 shows a diagramatic plan view of the device in its non-ambulant mode.
Figure 2:
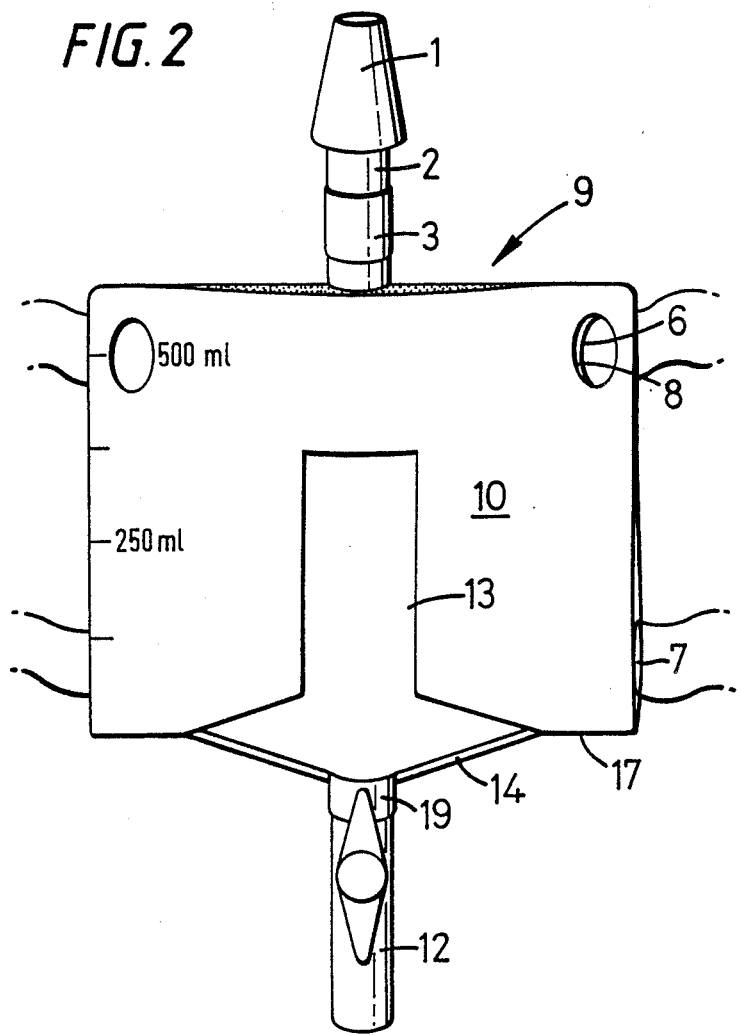
FIG. 2 shows a diagramatic plan of the device in its ambulant mode.

Referring to FIGS. 1 and 2 the urinary drainage device shown generally at (9) is provided with an inlet connector (1) formed with a tubular portion (2) which can be of varying length and which is bonded to an inlet tube (3) of the drainage bag (9). At the end of the inlet tube (3), and sealed within the bag (9), is a non-return valve (4) to prevent the reflux of urine.

The drainage bag (9) is provided with graduations (15) ideally up to 1000 ml, although greater or lesser values can be used where necessary. The drainage bag (9) is formed of a plastics material being separated into two chambers by a welded area (14); an upper chamber (20) and a lower chamber (10) each chamber being adapted to accommodate approximately 500 ml of liquid.

To either side of the weld (14) is an opening (17) which allows transfer of liquid to and from chambers (10 and 20) as necessary. At or towards the base of the chamber (20) is an opening (18) into which an outlet tube (19) is welded, said tube (19) being provided with a tap or valved outlet (12) as hereinafter described.

The drainage bag contains three pairs of opposed strap holes (6, 7 and 8) respectively at top, middle and bottom levels. These strap holes are adapted to accommodate straps (16) securing the device to the leg or waist of a patient.

Adjacent the upper edge of the upper chamber (20) a means of attachment (5), for example a strip of a hook and loop material "VELCRO", a registered trademark is attached to a corresponding attachment means (11), for example "VELCRO" strips, positioned at or adjacent the horizontal boundary of the lower chamber (10) when the lower chamber is to be arranged so that the drainage bag can be used as a 500 ml day bag. As an alternative to the "VELCRO" strips, plastics studs may be provided for inter-engagement with corresponding apertures.

The lower chamber (10) passes over a valved outlet (12) by means of a cutout (13) in the lower chamber thereby it may overlie, and abut against, the upper chamber (20) more closely. The drainage bag (9) is preferably formed of an opaque or semi-opaque or translucent plastics sheet material, preferably one which is readily heat-welded.

The surface of the bag (9) is provided with graduations (15) and other written matter embossed or printed in the plastics sheet material.

FIG. 2 shwos the bag (9) with the lower chamber (10) folded upon, and in overlying abutment with the upper chamber (20). The attachments (5) and (11) co-operate to retain this configuration in the day mode.

In use a catheter (not shown) is connected to an inlet connector (1) in a substantially permanent fashion. The drainage bag (9) is then secured in the mode shown in FIG. 2 to the leg of a patient by means of straps (16) passing through the apertures (7 and 8) and being tied about the leg of the patient. Alternatively, the drainage bag (9) may be supported by a waist band.

The valved outlet (12) is then shut off and urine is allowed to trickle via the non-return valve (4) into the chamber (20) where it is retained by valve (12). Of course some urine may make its way into a portion of the lower bag (10) which is upwardly folded upon the surface of the upper bag (20), but the capacity of the lower bag in the upwardly folded position is much reduced.

In the position as shown in FIG. 2 the upper chamber (20) may be voided by utilisation of the valved outlet (12) as desired.

At night, or when the patient has become non-ambulant, the lower chamber (10) may be downwardly pivoted to the position shown in FIG. 1. In this condition the liquid from the inlet (1) flows first into the lower chamber (10) and subsequently into the upper chamber (20). This gives a night time capacity of about 1 liter as opposed to a day time ambulant capacity of about one half liter.

Voiding of the bag as shown in FIG. 1 is effected by actuating the valved outlet (12) while pivoting the chamber (10) about its point of conjunction with chamber (20) so that both chambers are positioned superior to the valved outlet (12) thereby to allow all the liquid to flow out. Chamber (10) may then be returned to the position shown in FIG. 1 or attached as shown in FIG. 2.

In FIGS. 3 and 4 there is shown an alternative embodiment to FIGS. 1 and 2 wherein lower chamber (10) is not an integral part of upper chamber (20) but instead is a separate bag open about its top edge. In a separate welding operation the lower chamber (10) is conjoined to the upper chamber (20) by a horizontal weld interrupted adjacent one edge (23). The opening in the chamber (20) is thus operatively connected to the tap (12). Integers (21 and 22) indicate the join lines between the two chambers (10 and 20). The join can, of course be located anywhere between the top and bottom of the bag, but immediately adjacent the valve outlet (12) is preferred. The modus operandi of the arrangements of FIGS. 3 and 4 are in precise accord with the modus operandi of the arrangements shown in FIGS. 1 and 2. In an alternative form of the invention the valve outlet (12) is connected to the chamber (20) via a conduit (not shown) so that the outlet (12) is readily accessible to the hand for opening and closing when the bag is in its night-time mode.

FIG. 5 shows another variation in design which gives the facility for a high capacity day bag which can be attached to the leg by means of straps (16) in the usual way. It will be noted that the point of attachment of chambers (10 and 20) in FIG. 5 is vertical rather than horizontal and accordingly the "VELCRO" strips, or stud and aperture fixings, constituting the releasable fixing means are vertically rather than horizontally arranged.

The use of the device of FIG. 5 is analagous to the use of the arrangement of FIGS. 1 to 4.

It will be appreciated that in use the device shown in FIGS. 1 to 4 the top strap tends to remain in place, but the second strap can be placed in the middle for ambulant, or at the bottom for use as a "long day" bag.

The device of the present invention is provided with an outlet tap for draining the urine. The outlet tap is a crucial component of any drainage system and it is well documented that the outlet tap is the main point of entry for bacteria into any closed system (Aycliffe and Babb. Nursing Times 1986) and that cross action taps are the most susceptible in design to transfer infection to the bladder. Rotating taps are the least susceptible (Glenister H. Passage of Infection. Nursing Times June 3 Vol. 83 No. 22 1987).

It is similarly well documented that an outlet tap, particularly of a leg bag, should be operable with one hand only, and without the fingers coming into contact with any urine. (Roe, B. Evaluation of Urine Drainage System, Thesis 1986).

The outlet tap of the device in the invention is both a rotating tap in design and operable with one hand only without the fingers coming into contact with urine. This arrangement first assists the users with limited dexterity, and secondly makes it more readily possible to empty the contents of the bag.

The invention relates therefore to a body liquid drainage device particularly for urine and to an arrangement for preventing counter-current infection.

The word "VELCRO" used herein is a Registered Trade Mark.

I claim:

1. A body liquid drainage device comprising a first liquid storage chamber formed of a flexible plastic material and provided with an upper inlet for body liquids and a lower valved outlet for body liquids, a second flexible liquid storage chamber means movably connected to the first liquid storage chamber, said second chamber means being configured and movable for selective operation so as to be filled with the body liquid only when desired and to be emptied via said lower valved outlet for body liquids, such that when said second chamber means is folded over in overlying abutment with said first chamber, said valved outlet is disposed below said first chamber and said second chamber means.

2. A device according to claim 1 characterised in that the second chamber means is moveable from a first position in which it is generally in parallel abutment with the first chamber thereby to overlie the same in use, to a second position in which it forms an extension of the first chamber.

3. A device according to claim 2 characterised in that the second chamber means extends downwardly in use relative to the first chamber means whereby in the second position the valved outlet is positioned intermediate the length of the device.

4. A device according to claim 3 characterised in that the second chamber is formed with a cutout portion to accommodate the valved outlet.

5. A device according to claim 3 characterised in that the valved outlet is attached to the first chamber via a conduit.

6. A device according to claim 1 characterised in that the first chamber is provided adjacent its corners with opposed apertures to retain a body strap.

7. A device according to claim 1 characterized in that releaseable retaining means are secured to co-operating surfaces of the first chamber and second chamber means, thereby to fix said first chamber and second chamber means in overlying abutment in use.

8. A device according to claim 1 wherein the valved outlet is formed with a rotary valve adapted for single-handed operation.

9. A method for draining and storing body liquids in a body liquid storage bag, which method comprises the steps of: causing the body liquid to flow via an upper inlet into a first chamber provided with a lower valved outlet, said first chamber being sized for ambulant use, providing a second chamber means operatively connected to said first chamber and being adapted to be filled by said liquid in a non-ambulant mode concurrently or consecutively with said first chamber, and moving said second chamber means to a position wherein it is folded over in overlying abutment with said first chamber and said valved outlet is disposed below said first chamber and said second chamber means, so that said second chamber means can be emptied via the lower valved outlet.

10. A method according to claim 9 characterized in that the second chamber means is emptied with said first chamber in-situ on a patient by pivotal action of said second chamber means about a point of conjunction between the first chamber and second chamber means, whereby the second chamber means can be emptied without disconnection or use of a second valve.

* * * * *